(12) United States Patent
Wingfield

(10) Patent No.: US 10,687,535 B2
(45) Date of Patent: Jun. 23, 2020

(54) CHELATED METAL OXIDE GEL COMPOSITIONS

(71) Applicant: AG Tech LLC, Richmond, VA (US)

(72) Inventor: William Wingfield, Richmond, VA (US)

(73) Assignee: AG Tech LLC, Richmond, VA (US)

( * ) Notice: Subject to any disclaimer, the term of this patent is extended or adjusted under 35 U.S.C. 154(b) by 0 days.

(21) Appl. No.: 14/542,193

(22) Filed: Nov. 14, 2014

(65) Prior Publication Data

US 2015/0079141 A1     Mar. 19, 2015

Related U.S. Application Data

(63) Continuation-in-part of application No. PCT/US2013/000273, filed on Dec. 13, 2013.

(60) Provisional application No. 61/736,089, filed on Dec. 12, 2012.

(51) Int. Cl.

| | |
|---|---|
| *A01N 55/00* | (2006.01) |
| *A01N 25/02* | (2006.01) |
| *A01N 55/02* | (2006.01) |
| *A23B 4/22* | (2006.01) |
| *A01N 59/16* | (2006.01) |
| *A61K 33/24* | (2019.01) |
| *A61K 33/38* | (2006.01) |
| *A61K 33/34* | (2006.01) |
| *A61K 33/00* | (2006.01) |
| *A61K 31/765* | (2006.01) |
| *A61K 33/30* | (2006.01) |
| *A01N 59/20* | (2006.01) |
| *A61K 8/19* | (2006.01) |
| *A61K 8/73* | (2006.01) |
| *A61K 8/34* | (2006.01) |
| *A61Q 19/00* | (2006.01) |
| *A61Q 17/00* | (2006.01) |
| *A61K 8/02* | (2006.01) |
| *A01N 25/22* | (2006.01) |
| *A23L 3/3463* | (2006.01) |
| *A23B 4/24* | (2006.01) |

(52) U.S. Cl.
CPC ............ *A01N 55/02* (2013.01); *A01N 25/02* (2013.01); *A01N 25/22* (2013.01); *A01N 59/16* (2013.01); *A01N 59/20* (2013.01); *A23B 4/22* (2013.01); *A23L 3/34635* (2013.01); *A61K 8/0241* (2013.01); *A61K 8/19* (2013.01); *A61K 8/345* (2013.01); *A61K 8/736* (2013.01); *A61K 31/765* (2013.01); *A61K 33/00* (2013.01); *A61K 33/24* (2013.01); *A61K 33/30* (2013.01); *A61K 33/34* (2013.01); *A61K 33/38* (2013.01); *A61Q 17/005* (2013.01); *A61Q 19/00* (2013.01); *A23B 4/24* (2013.01); *A23V 2002/00* (2013.01); *A61K 2800/10* (2013.01); *A61K 2800/51* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 1,482,906 A | * | 2/1924 | Allen ........................ A61K 8/19 424/489 |
| 4,136,145 A | * | 1/1979 | Fuchs .................. A61K 9/7007 264/164 |
| 4,592,920 A | | 6/1986 | Murtfeldt et al. |
| 4,677,143 A | | 6/1987 | Laurin et al. |
| 4,847,049 A | | 7/1989 | Terry |
| 4,847,078 A | * | 7/1989 | Sheppard ................. A61K 8/26 424/78.25 |
| 4,849,223 A | | 7/1989 | Pratt et al. |
| 4,933,178 A | | 6/1990 | Capelli et al. |
| 5,019,096 A | | 5/1991 | Fox, Jr. et al. |
| 5,676,977 A | | 11/1997 | Antelman et al. |
| 5,848,995 A | | 12/1998 | Walder |
| 5,895,782 A | | 4/1999 | Overton et al. |
| 6,258,385 B1 | | 7/2001 | Antelman et al. |
| 6,583,176 B2 | | 6/2003 | Arata |
| 6,716,895 B1 | | 4/2004 | Terry |

(Continued)

FOREIGN PATENT DOCUMENTS

| | | |
|---|---|---|
| JP | 07-165510 A | 6/1995 |
| JP | 2007230996 A2 | 9/2007 |

(Continued)

OTHER PUBLICATIONS

Cheung et al., Chitosan: An Update on Potential Biomedical and Pharmaceutical Applications, Mar. Drugs 2015, 13, 5156-5186; doi:10.3390/md13085156 (Year: 2015).*

(Continued)

*Primary Examiner* — Jennifer A Berrios
(74) *Attorney, Agent, or Firm* — Myers Bigel, P.A.

(57) ABSTRACT

Described is a homogeneous gel composition with at least antimicrobial, antibacterial, and/or anti-viral properties comprising; a combination of a stable and homogeneous aqueous and/or polyol solution based chelated metal oxide liquid complex suspension and a gel composition free of chelated metal oxides comprising water, polyquaternium, glycerine and hyaluronic acid, wherein the homogeneous gel composition contains chelated metal oxide particles homogeneously suspended in the homogeneous gel composition such that a concentration of the chelated metal oxide particles contained within the homogeneous gel are in a concentration of at least 0.001 weight percent.

29 Claims, 2 Drawing Sheets

(56) References Cited

U.S. PATENT DOCUMENTS

| | | | |
|---|---|---|---|
| 6,756,059 B2 | 6/2004 | Terry | |
| 6,838,095 B2* | 1/2005 | Newman | A01N 59/16 424/618 |
| 6,881,421 B1 | 4/2005 | da Silveira et al. | |
| 6,916,468 B2* | 7/2005 | Lasota | A61K 8/042 424/70.11 |
| 6,949,598 B2 | 9/2005 | Terry | |
| 7,135,195 B2 | 11/2006 | Holladay et al. | |
| 7,179,849 B2 | 2/2007 | Terry | |
| 7,262,179 B2* | 8/2007 | Court | A61K 31/728 514/54 |
| 7,311,927 B2 | 12/2007 | Miner et al. | |
| 7,378,156 B2 | 5/2008 | Terry | |
| 7,700,131 B2 | 4/2010 | Taylor et al. | |
| 8,034,454 B2 | 10/2011 | Terry | |
| 2002/0192311 A1 | 12/2002 | Sakai | |
| 2004/0009210 A1* | 1/2004 | Koenig | A61L 15/225 424/445 |
| 2004/0022868 A1 | 2/2004 | Antelman et al. | |
| 2004/0043048 A1* | 3/2004 | Nomura | A61K 8/19 424/401 |
| 2004/0043963 A1* | 3/2004 | Wadstein | A61K 8/361 514/55 |
| 2005/0158405 A1 | 7/2005 | Boukas | |
| 2005/0250194 A1 | 11/2005 | Taylor et al. | |
| 2006/0074029 A1* | 4/2006 | Leece | A61K 8/34 514/23 |
| 2006/0105057 A1 | 5/2006 | Antelman et al. | |
| 2007/0264204 A1 | 11/2007 | Noor et al. | |
| 2008/0045491 A1 | 2/2008 | Fitchmun | |
| 2008/0311206 A1 | 12/2008 | Student et al. | |
| 2009/0018190 A1* | 1/2009 | Ebert | A61K 9/0014 514/534 |
| 2009/0035342 A1* | 2/2009 | Karandikar | A01N 25/34 424/411 |
| 2010/0120915 A1 | 5/2010 | Beierle | |
| 2010/0316749 A1* | 12/2010 | Fossel | A61K 8/0208 424/760 |
| 2013/0022643 A1* | 1/2013 | Sternoff | A61K 31/722 424/400 |
| 2013/0224308 A1* | 8/2013 | De Windt | B08B 7/0014 424/616 |
| 2014/0314820 A1 | 10/2014 | Wingfield | |
| 2015/0079141 A1 | 3/2015 | Wingfield | |
| 2015/0351406 A1 | 12/2015 | Wingfield | |
| 2015/0373984 A1 | 12/2015 | Wingfield | |

FOREIGN PATENT DOCUMENTS

| | | |
|---|---|---|
| JP | 2010202561 | 9/2010 |
| JP | 2012177901 A | 9/2012 |
| KR | 7090732 A | 9/2007 |
| RU | 2271814 | 3/2006 |
| RU | 2314796 | 1/2008 |
| WO | 2004028461 | 4/2004 |
| WO | 2006015317 | 2/2006 |
| WO | 2006/074359 | 7/2006 |
| WO | 2006/094387 | 9/2006 |
| WO | 2014092747 A1 | 6/2014 |

OTHER PUBLICATIONS

Chelate, https://science.jrank.org/pages/1375/Chelate.html, retrieved online on Jun. 21, 2019 (Year: 2019).*

Janssem, D.E. et al. "4-Iodoveratrole", *Organic Syntheses*, 4:547 (1963).

Hu, Z. et al. "Suspension of Slyer Oxide Nanoparticies in Chitosan Solution and its Antibacteriai Activity in Cotton Fabrics", *Mater. Res. Soc. Symp. Proc. Vol.*, 920:6 (2006).

Muzzarelli, R.A.A. et al. "Solubility and structure of N-carboxymethyichitosan", *Int. J. Biol. Macromol.*, 16:177-180 (1994).

International Search Report and Written Opinion, PCT/US2013/000273, dated May 22, 2014, 8 pages.

International Search Report and Written Opinion, PCT/US2015/060507, dated Mar. 22, 2016, 7 pages.

International Preliminary Report on Patentability and Written Opinion corresponding to International Application No. PCT/US2016/040294, dated Jan. 30, 2018, 6 pages.

Extended European Search Report corresponding to European Application No. 15859742.7 (16 pages) (dated Jul. 2, 2018).

Desbriers et al. "Surfactant-Chitosan Interactions and Application to Emulsion Stabilization" Cellulose Chemistry and Technology, 44(9):395-406 (2010).

Goycoolea et al. "Chitin and chitosan" Developments in Food Science, 41:265-308 (2000) (Abstract only).

Lu et al. "Preparation of Strong Cationic Chitosan-graft-Polyacrylamide Flocculants and Their Flocculating Properties" Industrial & Engineering Chemistry Research, 50(12):7141-7149 (2011) (Abstract only).

Nicu et al. "Chitosan as Cationic Polyelectrolyte in Wet-End Papermaking Systems" Cellulose Chemistry and Technology, 45(1-2):105-111 (2011).

Pranantyo et al. "Chitosan-Based Peptidopolysaccharides as Cationic Antimicrobial Agents and Antibacterial Coatings" Biomacromolecules, 19(6):2156-2165 (2018) (Abstract only).

Chinese Office Action and English Translation thereof issued for related Chinese Patent Application No. 201580073457.8 (28 pages) (dated Apr. 24, 2019).

"Cosmetic Pharmacology (2nd Edition)", Yang Tong et al, pp. 316-317, China Medical Science Press (Apr. 2007).

"Summarization of Pharmaceutical Adjuvant", Xi Nianzhu et al, pp. 473-474, Sichuan Science and Technology Press (Jan. 2006).

* cited by examiner

| 10 | Prepare Chitosan Solution |
|----|-------------------------------|
|    |                               |
| 11 | Provide deionized water       |
| 12 | Provide Chitosan powder       |
| 13 | Provide alpha-hydroxy acid    |
| 14 | Mix                           |

FIG. 1

| 20 | Prepare Aqueous Silver Solution |
|----|-------------------------------------|
|    |                                     |
| 21 | Provide silver oxidate              |
| 22 | Becomes alkaline solution in water  |
| 23 | Create silver oxide solution (from 21 and 22) |
| 24 | Create carboxylic acid solution with citric acid |
| 25 | Mix with deionized water            |
| 26 | Finalize chelated silver oxide solution and put into light resistant container |

FIG. 2

| 30 | Infuse Antimicrobial Complex into Gel to prepare Gel composition |
|---|---|
| | |
| 31 & 32 | Provide Chitosan Solution and DI water |
| 33 | Provide Aqueous Chelated Silver |
| 34 | Mix until Homogenous |
| 35 | Add to Gel to Finalize Gel Composition |

FIG. 3

CHELATED METAL OXIDE GEL COMPOSITIONS

This application is a 35 U.S.C. § 371 national phase application of International Application No. PCT/US2013/00273, filed Dec. 12, 2013, which claims the benefit, under 35 U.S.C. § 119(e), of U.S. Provisional Application No. 61/736,089, filed Dec. 12, 2012, the entire contents of each of which are incorporated by reference herein.

FIELD OF THE INVENTION

The present invention relates to a microbial, bacterial, viral, fungal, and mold resistant substance which includes a chelated metal oxide complex, and in particular, a stable chelated silver oxide solution suspended in a polyol-based aqueous gel. More specifically, the present disclosure describes adding a stable polyol-based chelated silver oxide solution into a gel composition comprising water, polyquaternium, glycerine, and hyaluronic acid, where the chelated metal (silver) oxide particles exist as a stable complex suspension in solution with the polyol and subsequently within the final gel composition. The polyol based aqueous solution and gel are both stable in that the chelated metal oxide does not precipitate out of the polyol solution for at least 6 months or longer and in most cases, depending on concentration, indefinitely.

The present disclosure also provides for use of the polyol chelated metal oxide complex, which is formed in the liquid state to be used in combination with other fluids or gels to impart the special properties associated with the same chelated metal oxides for additional uses. The polyol chelated metal oxide complex acts as a carrier for essentially any host that is compatible with the polyol. The polyols of the present disclosure are versatile and can be incorporated into at least gels as well as liquids and solids all of which are stabile up to the decomposition temperature of the polyol. In some cases, the polyols may also be useful as a carrier in a gaseous phase of the desired composition.

BACKGROUND OF THE INVENTION

For many years silver and silver salts have been used as antimicrobial agents. Early medicinal use of silver was the application of aqueous silver nitrate solutions to prevent eye infection in newborn babies. Silver salts, colloids, and complexes have also been used to prevent and to control infection. For example, colloidal metallic silver has been used topically for dermatitis, conjunctivitis, and infections including vaginal infections.

Other metals, such as gold, zinc, copper and cerium, have also been found to possess antimicrobial properties, both alone and in combination with silver. These and other metals have been shown to provide antimicrobial behavior even in extremely low concentrations, a property referred to as "oligodynamic." Metal ions, especially those of heavy metals, show this effect. The exact mechanism of action is still unknown. Data from silver suggest that these ions denature enzymes of the target cell or organism by binding to reactive groups, resulting in their precipitation and inactivation. There is recent evidence of changing the cellular DNA structure itself. Silver also reacts with the amino-, carboxyl-, phosphate-, and imidazole-groups and diminish the activities of lactate dehydrogenase and glutathione peroxidase. Bacteria are in general affected by the oligodynamic effect and it seems this effect is agnostic with regard to the strain of bacteria. Viruses in general are not as sensitive to this effect.

Silver is a naturally occurring element that is present in our environment, including the air we breathe, the water we drink and the foods we consume. However, silver does not occur naturally in the tissues of humans and animals. Silver's relatively low toxicity to animals and humans. It is however, extremely toxic to simpler forms of life such as bacteria. The antibacterial properties of silver are known, and were at least suspected for thousands of years. The ancient Greeks used silver pots and other utensils. Hippocrates, the father of modern medicine, wrote that silver had beneficial healing and anti-disease properties. The Phoenicians stored water, wine and vinegar in silver bottles to prevent spoiling. In the early 1900s, it was not uncommon for people to place silver dollars in milk bottles to prolong the freshness of the milk. The malleability and non-toxicity of silver make it a useful material used in dental alloys for fittings and fillings.

Widespread use of silver declined with the development of modern antibiotics, many of them used to kill pathogens, but overuse has led to increased bacteria resistance. Hence, there is renewed interest in silver as a broad spectrum antimicrobial. Silver, when applied topically, demonstrates efficacy against microorganisms which sometimes exhibit resistance characteristics. There are many products on the market to treat or kill bacteria. These products are found in a variety of forms, including liquid, foam, gel, lotions and ointments.

Additionally, silver is known for antimicrobial use with dental and medical devices, such as mouthpieces, mouthguards, dental appliances, as well as catheters, cannulae, and stents. Additionally, silver compounds have been used in fluids for consumption and incorporated into both clothing and packaging for prevention of infections, bacterial growth, and spoilage.

Hospital acquired infections due to bacteria cause approximately more than 100,000 deaths annually. This number is more than the combined death total resulting from AIDS, breast cancer and automobile accidents. The economic burden is estimated to be greater than $5.2 billion annually. These infections are the fourth leading cause of death. Inadequate hand hygiene also contributes to food-related illnesses, including *Salmonella* and *E coli* infection. According to The Center for Disease Control and Prevention (hereafter, the "CDC"), as many as 76 million Americans contract a food-borne illness each year. Of these, nearly 5,000 die as a result of the illness. Others experience the annoying symptoms of nausea, vomiting and diarrhea.

Published CDC guidelines enhanced hand sanitizer sales in the United States, which experienced double-digit growth in the 2004-2010 period, according to marketing information provided by A. C. Nielsen. The total annual U.S. infection prevention industry is estimated to be $9.4 billion.

With many devices, it is preferred to have a lubricious coating on the device. Lubricious coatings aid device insertion, reduce the trauma to tissue, and reduce the adhesion of bacteria. Another drawback to conventional methods which apply silver and other metals directly onto the surface of a device for which a lubricious coating is also desired is that a second, lubricious coating must be applied to the device over the antimicrobial coating, adding to manufacturing cost and time.

Some of these coatings release, to varying degrees, silver ions into the solution or tissue surrounding the substrate.

An oligodynamic metal may be physically incorporated into a gel in a variety of ways. For example, a liquid solution of a silver salt may be dipped, sprayed or brushed onto and into mammalian skin.

Settling of particles of the oligodynamic agent occurs as a result of the size and density of the particles. Settling of the particles from such solutions can cause unpredictable changes in the concentration of the oligodynamic agent in the composition. These changes in ion concentration result in several drawbacks for producing commercial products. First, unpredictable changes in the concentration of the oligodynamic agent make it difficult to produce a composition having a specific, homogenous, exact concentration of antimicrobial ions and, thus, a particular and specific effectiveness. Additionally, these changes make it difficult to produce multiple batches of the composition having the same antibacterial concentration. Furthermore, the concentration of the antimicrobial ions can affect other properties of the composition, such as its adhesive and lubricious properties. Consistency of antimicrobial activity is essential in the production of antimicrobial devices.

Another problem associated with particle suspensions is agglomeration of the particles. Particle agglomeration produces larger particle sizes which increases settling of particles from solution.

Many researchers have attempted to overcome these problems.

U.S. Pat. No. 4,847,049 to Yamamoto and entitled "Method of Forming Chelated Collagen Having Bactericidal Properties" describes a method for protecting renatured collagen against bacterial and fungal attack. The method includes contacting the collagen with a silver ion containing solution at a pH range of 4.0 to 9.0 and exposing the silver-chelated collagen to ultraviolet radiation.

U.S. Pat. No. 7,135,195 to Holladay et al. entitled "Treatment of Humans with Colloidal Silver Composition" describes water and silver particles, wherein the silver particles comprise an interior of elemental silver and an exterior of ionic silver oxide. The silver particles are described to be present in the water at a level of about 5-40 parts per million (Hereafter, "ppm").

U.S. Pat. No. 6,881,424 to Kemp entitled "Highly Acidic Metalated Organic Acid" teaches how to mix a monovalent or polyvalent cation and an organic acid in the presence of a strong oxyacid. The resulting composition is described to be less corrosive to a ferrous metal than a solution of a mineral acid having the same acidic pH value, and is more biocidal than a mixture of the organic acid and a metal salt of the organic acid which mixture has the same acid normality value.

U.S. Pat. No. 5,895,782 to Overton et al. is entitled "Acid Replacement Solution for Cleaning of Non Ferrous Metals" describes the use of non-ferrous alloys such as copper, brass and high strength aluminum alloys for cleaning purposes. The solution is described to be prepared by mixing Ca(OH)2 and KOH with equivalent sulfuric acid in water, and then passing the solution through a 10 micron filter.

U.S. Pat. No. 6,383,095 to Newman, et al. is entitled "Ionic Silver Complex" and describes how to combine ingredients including water, a source of free silver ions, and a substantially non-toxic, substantially thiol-free, substantially water soluble complexing agent. This patent claims the use of an alkali metal and/or alkaline earth metal used as a counter-ion.

U.S. Pat. No. 6,583,176 to Arata is entitled "Aqueous Disinfectant" and describes an aqueous solution that is formulated by electrolytically generating silver ions in water in combination with a citric acid.

Japanese patent application JP 2007230996A2 (Abstract only) and entitled "Anti-chafing composition comprising Boron Nitride" to General Electric Co., describes an anti-chafing composition for topical application comprising boron nitride.

US Patent Application No. 20080311206A1 entitled "Anti-Chafing Compositions Comprising Boron Nitride" to Student, et al. and assigned to General Electric Co., describes an anti-chafing composition for topical application comprising boron nitride.

U.S. Pat. No. 5,676,977 entitled "Method of Curing AIDS with Tetrasilver Tetroxide Molecular Crystal Devices" to Antelman and assigned to Antelman Technologies Ltd. describes a method of curing the AIDS virus using an intravenous injection using Tetrasilver Tetroxide.

Korean Patent Application KR7090732A—entitled "Anti-chafing compositions comprising Boron Nitride" to Student, et al. and assigned to General Electric Co., describes an anti-chafing composition for topical application.

U.S. Pat. No. 6,258,385 entitled "Tetrasilver Tetroxide Treatment for Skin Conditions to Antelman and assigned to Marantech Holding, LLC describes an invention that relates to the use of electron active molecular crystals comprising tetrasilver tetroxide (Ag4O4) for the treatment and cure of dermatological skin conditions.

US Application Number US20060105057 entitled "Compositions Using Tetrasilver Tetroxide and Methods for Management of Skin Conditions Using Same" to Antelman and assigned to Marantech Holding, LLC., describes pharmaceutical compositions including tetrasilver tetroxide (Ag4O4), such as in crystalline form, and methods of using such compositions for the prevention, treatment, and management of various dermatological skin conditions and diseases to include but not limited to skin chafing.

US Application Number US20040022868 entitled "Compositions Using Tetrasilver Tetroxide and Methods for Management of Skin Conditions Using Same" to Antelman and assigned Marantech Holding, LLC describes pharmaceutical compositions including tetrasilver tetroxide (Ag4O4), such as in crystalline form, and methods of using such compositions for the prevention, treatment, and management of various dermatological skin conditions and diseases to include but not limited to skin chafing.

US Application Number 20100120915A1 entitled "Antimicrobials and Related Methods to Beierle and not assigned, describes antimicrobial balms but does not mention the use of any type of silver or silver ions).

U.S. Pat. No. 7,311,927 entitled "Antiseptic Solutions Containing Silver Chelated with Polypectate and EDTA" to Miner, et al and assigned to Edwin Odell Miner, describes a liquid antiseptic and cleanser having improved long-term stability and includes silver ion in the list of ingredients.

PCT Publication Number WO2004/028461 entitled "Antiseptic Solutions Containing Silver Chelated with Polypectate and EDTA" by Miner, et al, describes a liquid antiseptic and cleanser having improved long-term stability and includes silver ions in the list of ingredients.

A PCT application to Karandiakar, WO 2006/015317, entitled "Antimicrobial Devices and Compositions" describes methods and compositions for antimicrobial devices comprising metal containing compositions which are resistant to heat and light discoloration. The metal containing compositions may comprise salts or complexes of silver, copper or zinc. In one aspect the compositions comprise silver salts. In another aspect, the compositions comprise silver complexes. In one aspect, the metal salts may comprise metal salts of saccharin, acesulfame, long chain fatty acids, and alkyl dicarboxylic acids. The compositions further comprise polymers which form salts or complexes with silver, copper or zinc. The methods of the present invention comprise treating devices with the metal containing compositions, including, but not limited to, such devices as woven wound care materials, catheters, patient care devices, and collagen matrices. A US Patent to Newman, U.S. Pat. No. 6,830,895, entitled "Ionic Silver Oxide Complex" describes an invention that relates to a substantially non-colloidal solution made by combining ingredients comprising (a) water; (b) a source of free silver ions; and (c) a substantially non-toxic, substantially thiol-free, substantially water-soluble complexing agent.

Therefore, a need has been established to provide a method for rendering a gel resistant to infection by reducing or eliminating undesirable bacteria growth primarily on the surface of the skin or for wounds or sores in the skin. It is important that the metal oxide complex is homogenously dispersed and endures throughout the life of the use of the gel and that the complex remains stable so that it can exhibit prolonged activity during shelf life. There is also a need in the art for metal oxide compositions which can be incorporated into gels to provide antimicrobial activity. There is also a need for compositions that overcome the solubility, settling, and agglomeration problems of conventional oligodynamic compositions, and exhibit enhanced, sustained release of oligodynamic agents when these agents (primarily silver oxide for the present disclosure, but copper and other metal oxides are also useful) are dispersed within gels, liquids and some solids. Incorporating the metal oxides into the products acceptable for mammalian skin application and even ingestion in a cost efficient and reproducible manner, is required for providing readily available items of manufacture and is one subject of the present disclosure.

SUMMARY OF THE INVENTION

Stated generally, the present invention comprises antimicrobial gel compositions which provide the advantage of the reduction or elimination of settling and/or agglomeration and/or precipitation by providing chelated metal oxide particles in a liquid homogenous dispersed suspension producing a minimal particle size of the oligodynamic metal oxides in the final gel composition. These particles remain suspended indefinitely in an the liquid dispersion prior to gelation in that they generally do not precipitate out of solution. The liquid portion of the solution is comprised primarily of a polyol and more specifically a glycerol and most specifically a water and/or glycerine and/or propanediol (vegetable or petroleum based) mixture. The use of metal oxide chelation in these compositions also permits incorporation of higher and more stable concentrations of these metal oxide particles without the difficulties associated with the suspensions described in the related art. The concentration of the silver oxide has been determined to allow for a stable (non-precipitate) form of the complex in solution that does not exceed 4000 ppm. These higher concentrations are important so that, eventually relatively lower (let down) concentrations of the chelated metal oxide dispersed suspensions can be added when preparing the gel compositions of the present disclosure. It is also possible to produce the final gel composition using lower concentrations of the metal oxide complex in solution.

Most specifically, described is an antimicrobial, antibacterial, and/or anti-viral, homogeneous gel composition comprising; a combination of a stable and homogeneous aqueous solution based chelated metal oxide liquid complex suspension and a gel composition free of chelated metal oxides, the gel comprising; water, polyquaternium, glycerine and hyaluronic acid, wherein the homogeneous gel composition contains chelated metal oxide particles homogeneously suspended in the homogeneous gel composition such that a concentration of the chelated metal oxide particles contained within the homogeneous gel composition are in a concentration of at least 0.001 weight percent.

The gel composition does not form a precipitate. The metal oxide particles in this case are normally silver oxide particles. The gel composition includes chelated metal oxide particles that initially comprise an alkaline aqueous silver oxide dispersion in that the initial addition of silver oxide particles into deionized and/or distilled water raises the pH of the water from between 5.5 and 7.0 to between 7.7 and 8.5. The initially aqueous dispersion is complexed with a combination of chitosan and carboxylic acid thereby providing chelated metal oxide particles.

The metal oxide of the chelated metal oxide particles are chelated silver oxide particles and the particle size distribution of the silver oxide particles is between 4 and 40 microns. The metal of the metal oxide particles can also be a group that consists of one or more of copper, zinc, titanium, gold, nickel, and tin oxide. The chelated metal oxide composition includes L-arginine, and a polymer of disaccharides. The disaccharides can include a polymer with hyaluronic acid.

Additionally, the chelated silver oxide particles are in a concentration of between 10 and 4000 ppm in the gel. The gel composition with the chelated silver oxide particles are more preferably in a concentration of between 100 and 250 ppm in the gel and most preferably at 250 ppm. The gel composition can be mixed into a gelled host where the gelled host can also be a polymer host and wherein the polymer can be a biopolymer.

Another embodiment includes that the gel composition is either mixed with and/or infused into, or otherwise used directly, as conditioners, hair mousse, hair spray, hair dye, contact lens solutions, deodorants, personal and industrial lubricants, food grade edible substances, water in the form of ice, skin lotions, topicals, toothpastes, oral gels, and alternatives to food grease. The gel of the gel composition is formed with any cationic system and the cationic system can be a cationic polymer system. Also, the cationic polymer system can be selected from the group consisting of alginate, chitosan, dextran, carrageenan, pectin, and xanthan gum.

The gel must be miscible and/or compatible with the polyol/glycerine based chelated metal oxide suspension so that combining the gel with the suspension leads to a final compound that achieves anti-bacterial and antimicrobial and in some case anti-viral properties. In making these compounds or final articles of manufacture, it also possible to include addition of other additives such as colorants (primarily azo compounds), inorganic elements, inorganic and organic compounds including clays, pigments, as fillers all without interfering or significantly altering the final antibacterial or physio-chemical properties of the eventual gel.

One particularly useful embodiment specifically provides an antimicrobial, antibacterial, and/or anti-viral, (as well as semi-conductive, inflammable, and reduced permeability) dispersing the following liquid composition in a gel, the liquid comprising; chelated metal oxide particles suspended in a polyol, wherein the metal oxide particles are homogeneously dispersed in the liquid and wherein the chelated metal oxide particles form a stable complex suspension that is often initially an alkaline based aqueous silver oxide dispersion complexed with a carboxylic acid, wherein the resulting metal oxide complex suspension is provided in a concentration of at least 0.001 weight percent in the liquid composition. The liquid composition is a stable suspension that does not form a precipitate. The liquid composition metal oxide complex is often most preferably silver oxide. The liquid composition of the polyol is often preferably glycerine. Further, the liquid composition can be an initially aqueous dispersion that is further complexed with a combination of chitosan and a carboxylic acid.

In a further useful embodiment, an antimicrobial, antibacterial, and/or anti-viral, gel composition comprises; chelated metal oxide particles homogeneously suspended in a polyol thereby creating a polyol chelated metal oxide complex suspension wherein the polyol complex is a carrier that is combined with a gelled host. The gelled host is a mixture of water (deionized or distilled is preferred, but most any purified water that is free of ions is useful) with a polyquaternium (such as Celquat H-100) with or without glycerine and hyaluronic acid and a biopolymer such as BHA-10 manufactured by Lipo Chemicals, Inc. (often referred to as beta hyaluronic acid) with the addition of a basic substance including but not limited to NaOH, $NaCO_3$, and/or arginine so that the final gel reaches a pH of at least 7.4. In providing the final gel product, the metal oxide (normally silver oxide) complex suspension is added to the gel an mixed in a mixer (planetary is one preferred mixer type) to produce a homogenous gel. The method by which the gel is accomplished ensures that no metal oxide precipitate occurs. The process of producing the gel ensures that the gel remains cationic—i.e. all the joins are positively charged—again to ensure that no AgO (or other metal oxide if a different meal oxide is used) precipitate forms.

In another aspect, the compositions of the present invention provide the advantage of varying release kinetics for the active oligodynamic ions due to different solubilities of different chelated metal oxides in the compositions. These varying release kinetics allow for an initial release of oligodynamic ions that provide antimicrobial activity immediately upon use, followed by a continual, extended release of the oligodynamic ions from the gel, resulting in sustained antimicrobial activity over time.

In yet another embodiment, antibacterial, antimicrobial, and/or antiviral products manufactured comprise a gel composition and chelated metal oxide particles homogeneously suspended in a polyol combined and infused into a polymer of the polymeric composition including a polyol metal oxide complex in a concentration of at least 0.001 weight percent metal oxide infused within the polyol such that the concentration of the polyol metal oxide complex is no greater than 25 weight percent of the polymeric composition.

A further embodiment of this invention results in a composition comprising a silver oxide and water and/or glycerine chelated silver oxide solution together with a co-complexing bio-film former in the gel wherein the gelled composition electrostatically binds with a negatively charged surface.

Embodiments of this invention are thereby achieved by the method of creating a metal oxide composition as disclosed within, the steps of which comprise providing a chelated oxide complex with a concentration of at least 1000 parts per million of silver oxide together with a polyol, which results in forming a chelated silver oxide polyol complex within a polyquaternium gel such that the chelated silver oxide concentration within the gel is at least 250 ppm.

DETAILED DESCRIPTION

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

The term "safe and effective amount," as used herein, means an amount of an applied compound, component, composition or complex to significantly induce a positive antibacterial/microbial/viral benefit to the user providing a reasonable benefit to risk ratio, within the scope of sound medical judgment.

The Composition of the Chelated Silver Oxide Solution

In a first aspect, the present invention provides antimicrobial, antibacterial, and in some cases, anti-viral metal oxide complexes in primarily aqueous and/or polyol based solutions forming stable homogenous chelated metal oxide complex gels exhibiting no precipitate.

In a second aspect, the complex oligodynamic agent suspension is direct injected, mixed, blended, or compounded with a gel. The term "oligodynamic agents" as used in the present disclosure refers in this case to any chelated metal oxide compound that provides an associated antimicrobial (or other desirable) characteristic or activity, even when present in relatively small quantities and low concentrations.

One preferred embodiment is that of a chelated silver oxide that is suspended in a polyol. The homogenous chelated metal (silver in one instance) oxide suspension is concentrated in the either a water or polyol (for example PEG—polyethylene glycol or glycerine) or a combination of both a polyol and water to 4000 ppm. Higher initial concentrations with, for example, PEG, are possible, but the primary focus is to provide chelated metal oxide (and in particular silver oxide) solutions that do not allow precipitate to form. This highly concentrated chelated metal oxide solution is a complex suspension that is subsequently diluted as it is incorporated into essentially any gel or other acceptable (miscible with the polyol carrier) liquid. This incorporation imparts the desirable properties of the chelated metal oxide into the host substrate without any intended or known undesirable physio-chemical property changes.

Any gel may be employed in the present invention, including hydrophilic gels, hydrophobic gels, and mixtures of these two types. The use of hydrophilic gels maybe preferred because such gels may have additional benefits. These benefits include increased lubricity for patient comfort, increased absorption of aqueous fluids from the body which aids in the release of oligodynamic ions from the composition, inhibition of bacterial attachment, and improved solubility for some metal oxide chelates. Hydrophilic gels best suited to the invention are those that are soluble in water or in organic solvents containing water. The ability to add water to the gels without precipitating the metal oxides is an added benefit but not a prerequisite of the present invention. Water facilitates the formation of salt colloids that may precipitate either before or after addition the gels providing the final composition. For this reason, it is preferred that the gel contain essentially no water by weight, and certainly no more than 5 to 30% water.

However, the use of water is not limiting, as metal oxide chelates can also be formed or suspended in alcohols, organic solvents, or both that contain little or no water. The use of alcohols and organic solvents, containing from 0 to 1% water are preferred when hydrophobic gels are employed in the present invention. Activity of the chelated metal oxides will vary with the carrier they are employed within. Precipitation will also vary based on the initial concentration of the metal oxide capability within the complex suspension.

Examples of hydrophilic food grade edible gels include those made using glycerine and an emulsifier such as describe in the U.S. Pat. No. 8,557,264 B2 to Grune, et al., the contents of which are hereby fully incorporated by reference. Petrolatum based gels are generally hydrophobic. It is possible to combine both hydrophobic and hydrophilic gels in the present invention. Final gel compositions may include essentially any inorganic or organic fillers that do not interfere with the antibacterial and antimicrobial behavior of the chelated silver (and other metal) oxides and can include some or all of the following organic polymers; polyurethanes, including polyether polyurethanes, polyester polyurethanes, polyurethaneureas, and their copolymers; polyvinylpyrrolidones; polyvinyl alcohols; polyethylene glycols and their copolymers; polypropylene glycols and their copolymers; polyoxyethylenes and their copolymers; polyacrylic acid; polyacrylamide; carboxymethyl cellulose; cellulose and its derivatives; dextrans and other polysaccharides; starches; guar; xanthan and other gums and thickeners; collagen; gelatins; and other biological polymers. Preferred hydrophilic polymers to be used in the hydrophilic gels include polyurethanes and polyurethane copolymers, such as polyether polyurethaneurea.

Examples of hydrophobic polymers best suited for use in hydrophobic gels (normally provided in a petrolatum base) include but are not limited to; polytetrafluoroethylene, polyvinyl chloride (PVC), polyvinylacetate, poly(ethylene terephthalate), silicone, polyesters, polyamides, polyureas, styrene-block copolymers, polymethyl methacrylate, acrylic-butadiene-styrene copolymers, polyethylene, polystyrene, polypropylene, natural and synthetic rubbers, acrylonitrile rubber, and mixtures and copolymers of any of the above.

The chelates of the present invention comprises one or more oligodynamic metal oxides. In the discussion of the process below the metal oxide is silver oxide, but copper, tin, aluminum, zinc, and titanium all form metal oxides that can be chelated. Oligodynamic metal oxides useful in the present invention include, but are not limited to, silver, platinum, gold, zinc, copper, cerium, gallium, osmium, and the like. For purposes of the present disclosure, the preferred oligodynamic metal is silver.

Chelation of other metals may be employed to form the chelate. Salts may act as partial chelating agents and contain cationic ions that include, but are not limited to, calcium, sodium, lithium, aluminum, magnesium, potassium, manganese, and the like, and may also include oligodynamic metal cations such as copper, zinc, and the like. These salts contain anions that include, but are not limited to, acetates, ascorbates, benzoates, bitartrates; bromides, carbonates, chlorides, citrates, folates, gluconates, iodates, iodides, lactates, laurates, oxalates, palmitates, perborates, phenosulfonates, phosphates, propionates, salicylates, stearates, succinates, sulfadiazines, sulfates, sulfides, sulfonates, tartrates, thiocyanates, thioglycolates, thiosulfates, and the like. The invention may also be practiced with oxides serving to form the chelates including, but not limited to, oxides of calcium, sodium, lithium, aluminum, magnesium, potassium, manganese, and the like, and may also include oxides of oligodynamic metals such as silver, copper, zinc, titanium and the like.

The compositions of the present disclosure can also contain any combination of additional medicinal compounds. Such medicinal compounds include, but are not limited to, antimicrobials, antibiotics, antifungal agents, antiviral agents, antithrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds, such as chlorhexidine and its salts; triclosan; penicillins; tetracyclines; aminoglycosides, such as gentamicin and Tobramycin (an aminoglycoside antibiotic derived from *Streptomyces tenebrarius*, polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity.

The gel compositions can also contain auxiliary components. Examples of such auxiliary components include, but are not limited to, viscosity and flow control agents, antioxidants, conventional color pigments, air release agents or defoamers, and discolorants. The gel composition may also contain conventional dyes and pigments to impart color or radiopacity to enhance the aesthetic appearance of the gels. The azodyes, in particular, have been added to the polyol chelated metal oxide complex carriers together with the gel host to provide enhanced colored appearance.

The gels can also contain additional lubricating agents and other additives that enhance patient comfort and tissue health. As previously mentioned, it is also possible to add any flavorant or flavoring to the polyol carrier prior, during, or after addition of the chelated metal oxide complex. These flavoring can be man-made (synthetic) or naturally occurring flavorants.

While not wishing to be bound by the following mechanism, it is believed that many of the advantageous properties of the present compositions result from the differences in the solubility of the different chelated metal oxides present in the polyol suspension. These differing solubilities of the metal oxides in the polyol are key in determining concentration levels and resulting precipitation as well as providing varying release kinetics for the active oligodynamic metal(s). For example, with a medical device composed of, or coated with, the compositions of the present invention, those chelates that have high water solubility will be released rather quickly, providing a high initial dose of antimicrobial activity to kill bacteria introduced upon insertion of the device in the patient. This initial dose is sometimes referred to as "quick kill," and this antimicrobial activity is identified by the ability of a device or composition to create zones of no bacterial growth around the device or composition when it is placed in a bacterial culture. This test is known as a "zone of inhibition" assay. Those chelates having lower polyol solubilities will be released more quickly from the hydrophilic composition, resulting in a sustained or extended antimicrobial activity over time.

Selection of chelated metal oxides having varying degrees of solubility in the composition allows tailoring of the composition to the specific application of the gel composition. Specifically, compositions of the invention can be tailored to kill bacteria introduced during topical or internal application for mammals and more specifically for humans by surrounding fluid and tissue using quick release of antimicrobial metal oxides, followed by prolonged inhibition of bacterial migration and growth. The ability to tailor the release of the oligodynamic agent is advantageous over conventional antimicrobial gel compositions, as it provides for both immediate and sustained antimicrobial activity.

Another advantage of the compositions of the present invention is that the formation of chelates suspended in polyols within the gel compositions that produces ultra-fine particles that possess a minimal particle size for the metal oxides. The original size of the silver oxide particles for the present invention are in the order of 4 to 40 microns in terms of particle size distribution. This minimal particle size distribution retards settling and agglomeration but is large enough so that the particles are not considered to be nano-sized. The use of suspended chelates in the composition also permits incorporation of higher quantities of antimicrobial metal oxides without the difficulties associated with other related art.

By reducing or eliminating the problems associated with conventional antimicrobial gel compositions, the present invention provides reproducible compositions having a specific antimicrobial chelated metal oxide concentration with a specific antimicrobial ion release profile that can be tailored through the specific combinations selected to provide optimum antibiotic activity over an extended period of time. For example, compositions of the present disclosure can be tailored to release the bulk of their oligodynamic agents within 1 hour or up to 5 day. By changing the initial relatively high concentration of the chelated metal oxide in the polyol, the final polymeric composition of matter can be tailored to a specific concentration of metal oxide. The initial release and the duration of release of the oligodynamic agents from the composition depend upon several factors. These factors include the relative solubilities of the particular chelates formed in the suspension, the concentration of the metal oxides in the suspension (carrier), and at least the phase (liquid-like or solid-like), density, and the chemistry of the gel host material. This release can be tailored through the choice and number of metal oxide chelates formed in the composition for the intended purpose of the manufactured gel.

To more completely define what is meant by polyols, the following explanation applies throughout the present specification and claims. Namely, sugar alcohols, a class of polyols, are commonly added to foods because of their lower calorific content than sugars; however, they are also, in general, less sweet, and are often combined with high-intensity sweeteners. They are also added to chewing gum because they are not broken down by bacteria in the mouth or metabolized to acids, and thus do not contribute to tooth decay. Maltitol, sorbitol, xylitol and isomalt are some of the more common types. Sugar alcohols may be formed under mild reducing conditions from their analogue sugars. These polyols can be used to provide the dispersed suspension of chelated metal salts of the present invention.

In polymer chemistry, polyols are also known and are specific to compounds with multiple hydroxyl functional groups (which are generally available for organic reactions). A molecule with two hydroxyl groups is a diol, one with three is a triol, one with four is a tetrol and so on.

Monomeric polyols such as glycerine, pentaerythritol, ethylene glycol, and sucrose often serve as the starting point for polymeric polyols. These materials are often referred to as the "initiators" and can be reacted with propylene oxide or ethylene oxide to produce polymeric polyols including polyethylene glycol. However, they should not be confused with free radical "initiators" used to promote other polymerization reactions. The functional group used as the starting point for a polymeric polyol need not be a hydroxyl group; there are a number of important polyols which are suitable for providing amine functionality. A primary amino group (—NH2) often functions as the starting point for two polymeric chains, especially in the case of polyether polyols.

Polymeric polyols are often used to produce other polymers. They can be reacted with isocyanates to make polyurethanes used to make mattresses, foam insulation for appliances (refrigerators and freezers), home and automotive seats, elastomeric shoe soles, fibers (e.g. Spandex), and adhesives.

Polymeric polyols are usually polyethers or polyesters. Polyether polyols are made by reacting epoxides like ethylene oxide or propylene oxide with the multifunctional initiator in the presence of a catalyst, often a strong base such as potassium hydroxide or a double metal cyanide catalyst such as zinc hexacyanocobaltate-t-butanol complex. Common polyether diols are polyethylene glycol, polypropylene glycol, and poly(tetramethylene ether) glycol. The examples shown below are fairly low molecular weight triols based on glycerine (a triol). Polyether polyols account for about 90% of the polymeric polyols used industrially; the balance are polyester polyols.

Another class of polymeric polyols are the polyesters. Polyesters are formed by condensation or step-growth polymerization of diols and dicarboxylic acids (or their derivatives), for example diethylene glycol reacting with phthalic acid. Alternatively, the hydroxyl group and the carboxylic acid (or their derivatives) may be within the same molecule, as in the case of caprolactone. The example below is an idealized structure that could be obtained by reacting pentaerythritol (a tetrol) with gamma-butyrolactone.

Hydroxyl-terminated polybutadiene is a polyol used to produce polyurethane. Polyester polyols from vegetable oils, known as natural oil polyols or NOPs, are replacing some epoxide-based polyols and can also be used for making the dispersed metal oxide suspension "carrier" of the present invention.

All of the various forms and types of polyols listed above may be used for dispersing the chelated metal oxides and/or helping to form a gel composition containing a homogeneously dispersed chelated metal oxide substance (carrier) throughout the final gelled host. In the case of introducing silver oxide into polyols, it may be necessary, in order to provide higher concentrations of the silver oxide to first suspend the chelated silver oxide in water or glycerine or polyethylene glycol (PEG) and then incorporate the infused glycerine into the gel.

In one disclosed embodiment, the present disclosure comprises one or more chelated silver oxide forms as the oligodynamic agent which is combined with a liquid phase polyol or glycerine, producing a homogenous dispersed suspension of the chelated silver oxide in the gel. In another embodiment, the composition optionally contains additional chelated metal salts of other oligodynamic metals, such as zinc, gold, copper, cerium and the like. In still another embodiment, the composition optionally comprises additional chelated salts of platinum group metals such as platinum, palladium, rhodium, iridium, ruthenium, osmium, and the like. The compositions optionally contain any other components that provide beneficial properties to the composition or improve the antimicrobial effectiveness of the composition.

In a second aspect, the present invention relates to a process for producing these antimicrobial gel compositions. The process comprises the formation of chelates of oligodynamic agents in solutions, dispersions, or combinations of gels and dispersions. The chelated metal oxide suspension (a carrier in some cases) is formed first and then can be subsequently added to the gelled host to form another (new) composition or the chelated metal oxide complex can be formed in situ as the gel is formed.

One preferred embodiment is for the chelated metal oxide to be a silver oxide that is dispersed in glycerine and/or water prior to or during adding to the gel and optionally with colorant that is known to provide color without interfering with the processibility, color desired, or physio-chemical behavior of the final compound.

The final gel composition can therefore be either a one, two, or at least three component system; a chelated metal oxide suspension, the metal oxide suspension added to the gel, and the metal oxide, gel composition, and optionally incorporation of a colorant. Four or more component systems would include the additional incorporation of both organic and inorganic fillers such as antioxidants, other anti-bacterial compositions, flavorings, flame retardants, etc., which would impart special additional properties and benefits to the final gel composition.

It has also been found that the addition of the metal oxides in polymeric systems results in the ability of the gel compositions to become conductive or at least semi-conductive especially for membrane and wire and cable application. Additionally, the chelated metal oxides that are added into base gels will provide enhanced physio-chemical properties. An application for which the chelated metal oxides are of great benefit is UV resistance. Although normally associated with zinc oxide, chelated silver oxide also exhibits UV resistance. Use of chelated copper, nickel, tin, and aluminum oxides may provide better economic benefits for some of the products that can be formed from these compounds. These associated properties for the two or more component gel systems are also part of the present disclosure.

In most, if not all cases, the polymer physio-chemical, physical, and/or mechanical properties without the chelated metal oxides are either not compromised or not substantially compromised in comparison with the identical gel composition that does not have the chelated metal oxides compounded into the system from the metal oxide complex (carrier system). This is also a very important and distinguishable characteristic of the present invention. In terms of commercial value, the fact that unique properties can be incorporated into gel compositions with relatively minor added costs based on very low concentrations (normally less than 1000 ppm) of the metal oxide, provides a very distinct advantage over any known gel additive technology, especially for the incorporation of silver oxides.

Use of gels for the present disclosure (chelated metal oxides formed within polymer) include almost too many to list. The list given below is not intended to be all inclusive, but has been separated based on desirable parametric attributes.

For antibacterial, antimicrobial, antiviral, anti-fungal and anti-mold gels, the desired articles of manufacture include at least the following;

Medical and hospital use of the gels in conjunction with or separate from tubing, masks, mats, plastic cups, surgical instruments, etc., which also include, but are not limited to, catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, wound dressings, as well as breathing masks and essentially any product that comes into contact with the skin or provides a mechanism for filtering gases of liquids inhaled or ingested by humans. The need for reducing or eliminating "staph infections" in the medical community is well known and the gels of the present invention have been proven to provide these properties without sacrificing other physio-chemical attributes. This is in part due to the nature of adding relatively low (ppm) concentrations of the chelated metal oxides.

Use of the gel with children's items, including toys, bottles, pacifiers, and essentially any article of manufacture made for infants or children also benefit greatly from the use of the gels of the present disclosure.

Also included are gels that include incorporation of the food edible glycerine gels containing the chelated silver oxide that can be infused into any liquid or solid food substance. The chelated silver oxide is not only GRAS (generally accepted as safe) but is also non-toxic and meets any FDA requirements, so that it can be used with glycerine to establish many novel and unique items for animal and human ingestion (solid foods, liquid foods, and drinks including water and ice).

Other home products where the gels may find usefulness include bathroom accessories such as bathroom fixtures, flooring, cleaning products, air filtration items, food storage items HVAC, luggage and office and school products. Toilet seats and portable toilets (including those for aircraft and automotive use) are areas associated with high level of bacteria that would also benefit from the technology described herein.

The chelated metal oxide in polyols are suitable (both with and without compounding with the gels) for use in paints, personal care products, pool and spa products, grout and sealants as well as for adhesives and generally anywhere inside or outside the home or industrial/commercial buildings where mold and/or mildew is a source of concern.

Sporting equipment can also benefit by the addition of these gels such as mouthguards, mouthpieces, and in general, dental appliances. The use of chelated silver oxide as a substance which can be ingested (as opposed to other forms which are in carriers that are inappropriate for injection—such as clay nano-particles and other solid forms of the silver oxides) provide opportunities for applications of products designed to be ingested or used with already FDA approved articles of manufacture for human exposure. The chelated metal oxide gel composition in a vegetable based glycerine base is useful for essentially any food products and could even be combined with water in any form—including ice—such that the food and water (or any water based substance) will exhibit antimicrobial/antibacterial and antiviral properties. Certainly there is ubiquity involved regarding the many food, food preparation and fluid consumption applications (including beverages) for just the glycerine based gel complex which can be added to essentially all food and beverage items (including all known baked goods) as it is non-toxic, "green" and sustainable and food-grade ingestible. "Green", in this sense refers to a large number of products now being touted as either organic and/or non-toxic and/or earth grown or earth derived substances that will not cause toxic waste when manufactured, used, and/or disposed. The concept of "cradle to cradle" or "cradle to grave" for products using Life Cycle Assessment tools to determine the validity of the term "green" is, in part, a methodology with which the inventors have experience and is useful in further defining "green" products.

In addition, the same glycerine or water based chelated silver oxide gel complex can be added directly to flavorings and flavored items. In some cases, this could include flavored gel substances that are treated with the chelated silver oxide carrier.

Baby changing stations, cleaning supplies, commercial high chairs, dispensers, door hardware (including knobs), electronics, elevators, storage units, surface coatings, and transportation products of all types will also benefit from the technology described herein. Yoga and wrestling mats are also articles of manufacture covered by the present disclosure.

For automobile interiors there are numerous applications for the gels that include use with steering wheels and covers, window handles and buttons, dashboards, radio and navigation controls, etc.

All forms of communications devices including cell phones and all the peripheral equipment regarding such, personal computers, mobile devices, tablet devices (iPad, etc.), are all articles of manufacture that will benefit from the use of the antibacterial properties assured by using chelated silver oxide fortified gel systems as described herein.

In another aspect, the present invention relates to an article of manufacture which comprises a substrate and the antimicrobial compositions of the gel. In a disclosed embodiment, the gel composition is employed in the manufacture of the article itself. Thus, the final article is composed of one or more of the gel compositions of the present invention, alone or in admixture or by application on or into other manufactured items.

Optionally, additional components can be added to the antimicrobial gel compositions of the present invention. These components include, but are not limited to, additional oligodynamic agents, additional soluble salts, and any other components which provide the gel compositions with beneficial properties or enhance the antimicrobial activity of the gel compositions without interfering with the basic gel properties. Such components include, but are not limited to, antimicrobial agents, antibiotics, and other medicinal agents.

All percentages and ratios used herein are by weight of the total composition and all measurements made are at 25 degrees Centigrade unless otherwise designated. Unless otherwise indicated, all percentages, ratios, and levels of ingredients referred to herein are based on the actual amount of the ingredient, and do not include solvents, fillers, or other materials which may be combined with the ingredient in commercially available products.

Described is an initial liquid composition with at least antimicrobial, antibacterial, and/or anti-viral properties comprising chelated metal oxide particles suspended in a polyol, such that metal oxide particles are homogeneously dispersed in the primarily liquid based polyol carrier and such that the chelated metal oxide particles form a stable complex suspension that can eventually become an alkaline based aqueous silver oxide dispersion. The suspension can be optionally further complexed with a combination of chitosan where the resulting metal oxide complex is provided in a concentration of between 0.1 and 25 weight percent. The liquid composition can be subsequently added to essentially any gel or gel composition/system. The metal oxide complex may also impart beneficial semi-conductive or conductive as well as permeability and flammability property changes to the gelled host.

The total amount of chelated silver oxide complex suspension formed in the polyol ("carrier") and eventually captured within the gel forming the antibacterial formulation (host) of the present invention may be varied within wide parameters, but should be in a sufficient amount for the composition to act as a germ-like barrier and provide a gel that effectively inhibits, reduces and essentially eliminates bacterial growth. The same holds true for imparting other properties including reducing permeability (particularly to oxygen), flammability, and increasing UV resistance.

Generally, in one embodiment, the anti-bacterial, antimicrobial, germ barrier effective amount of the chelated metal oxide in the polyol is generally in the range of 0.001 to 10 weight percent based on the total weight of the polyol formulation so that one can add smaller amounts and concentrations of the polyol carrier into a separate or concurrently formulated gel to form a resultant gel composition that possesses an antimicrobial effective amount of the silver oxide complex.

In another embodiment, the antimicrobial composition comprises at least one either aqueous or glycerine phase formulated chelated metal oxide solution, for example, in a form chosen from water-in-oil emulsions, oil-in-water emulsions, and multiple emulsions, e.g., oil-in-water-in-oil and water-in-oil-in-water triple emulsions.

In another embodiment, the at least one phase comprises polyol and generally other polyol soluble or miscible solvents. The solvents may be chosen from short-chain monoalcohols, for example, monoalcohols of C1-C4, such as ethanol and isopropanol; and diols and polyols themselves, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol.

In yet another embodiment, the carrier vehicle comprises propylene ethylene glycol and/or glycerol. Another useful component for preparing the antibacterial portion of the formulation is the use of propanediol.

In a further embodiment, the composition comprises at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20 to 25 degrees Centigrade).

In yet another embodiment, the at least one water-immiscible organic liquid phase is chosen to be the carrier for the chelated silver oxide and can be from an oil and/or a mixture of oils and comprising at least 80% of compounds with a vapor pressure not exceeding 4 kPa (30 mmHg) at 25 degrees Centigrade. The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463, hereby incorporated by reference.

As used herein, volatile silicones are defined, in a known manner, as being compounds that are volatile at room temperature. Mention may be made, for example, among these compounds, to cyclic and linear volatile silicones of the dimethylsiloxane type, whose chains comprise from 3 to 9 silicone-based residues. As used herein, non-volatile silicones are defined, in a known manner, as being compounds with a low vapor pressure at room temperature, such as polyalkylsiloxanes, such as linear polyalkylsiloxanes, including linear polydimethylsiloxanes, or dimethicones; polyalkylarylsiloxanes, for example, polymethylphenylsiloxanes; and copolymers of polyether and siloxane, for example, dimethicone copolyols. Among the non-volatile emollient oils that may be used, examples include hydrocarbon-based derivatives, mineral oils, fatty alcohols, esters of C3-C18 alcohols with C3-C18 acids, esters of benzoic acid with C12-C18 alcohols and mixtures thereof, C2-C2-C6 polyols, for example, chosen from glycerol, propylene glycol or sorbitol, polyalkylene glycol polymers.

Mixtures of carrier materials and/or surfactants are also usable as carriers for the chelated metal oxides. The total amount of carrier material employed is for some embodiments, from 1% to 99%, and for other embodiments, from 60% to 98%, expressed as a weight percentage of the total weight of the composition. The chelated metal oxide complex is normally added in amounts up to 250 to 1000 ppm by weight for most gel systems. For food and beverage the percentages are usually smaller.

In a separate embodiment, the antimicrobial compositions further include at least one other agent that imparts color or other aesthetics to the gel composition, including organic structurants that are non-polymeric or polymeric. Examples of non-polymeric structurants include, but are not limited to, colorants or dyes.

The antimicrobial chelated metal oxide component dispersed suspension can be dispersed in one or more of a selected group of gels that contain in most cases lower weight percent concentrations of any of the following including; polyvinyl alcohols, polyvinyl pyrrolidone, polyalkylene oxides, celluloses, cellulose derivatives, polysaccharides, polysaccharide derivatives, polycarboxylic acids, salts of polycarboxylic acids, polyamino acids, peptides, polyamides, polyacrylamides, polyesters, poly (vinyl methyl ether-co-maleic anhydride), alginates, alginate derivatives, pectins, polyethylene oxides, gelatins, carrageenans, chitosans, starches, starch derivatives, and combinations thereof. These "additives" can be in either the liquid or solid phase at room temperature or ambient conditions and capable of keeping the chelated metal solution suspension is stabile state so that blending, combining and/or compounding the dispersed chelated metal suspension into a gel matrix does not reduce or eliminate the antibacterial effects in the final gel composition used to manufacture the final gel composition.

The gel composition of the present invention also can comprise other components that may be chosen depending on the carrier and/or the intended use of the formulation in the gelled host. The optional components are used in an amount that does not substantially or adversely impact the desired anti-bacterial effect.

In addition to the preservative nature of the chelated metal oxide complex, another embodiment includes the use of at least one preservative compound in combination with the topical anti-chafing chelated silver oxide gel compositional material. The preservative compounds may be present in an amount of 0.5% to about 3% by weight of the formulation. Desirably, the preservative compound is effective against yeast, particularly *Candida albicans*; molds, particularly *Aspergillus niger*; and bacteria, particularly *S. aureus, E. coli*, and *E cloacae*. Examples include disodium ethylene diamine tetraacetic acid, methylparaben, and diazolidinyl urea. The chelated silver oxide complex also serves as a chelating agent to block the activity of bacterial ureases, lipases, proteases, and decarboxylases produced by *Klebsiella pneumoniae, Proteus mirabilis*, and *E. coli* bacteria In addition the chelated silver oxide can act as a preservative for pharmaceutical, antibiotic, and other medications.

In one other embodiment, the antibacterial polyol based metal oxide liquid complex suspension and final gel composition may also include fragrances. Examples include but are not limited to citrus, floral, spicy, lavender, woody, mossy, oriental, herbal, leather-tobacco, and aldehydic groups. Typically, fragrance materials are supplied as concentrates, which generally contain up to about 3 percent fragrance by weight. Examples include natural products such as essential oils, flower oils, natural extracts from resins, gums, balsams, beans, mosses and other plants, and animal products such as ambergris and musk, as well as synthetic aromatic materials.

Process for Preparing the Composition and Documented Results

In a first aspect, the present invention relates to a process for producing the compositions of the invention. In general terms, the process comprises the formation of suspended chelates of oligodynamic agents first prepared in polyols and simultaneously or subsequently added into already accomplished of forming gel compositions via mixing/blending/compounding with or without using pressure and/or heat. The chelated metal oxide suspension is normally formed first and then added to the gel composition or can be formed in situ during gelation.

This results in a polyol water or glycerine or PEG or a combination of all three based chelated silver oxide complex suspension that is a liquid at room temperature. The method to develop the liquid suspension requires following a procedure such as described below in Example 1.

Example 1

Procedure for Making 250 Ppm Homogeneous Chelated Silver Oxide Gel

The process of forming the chelated silver oxide for the polyol based liquid complex suspension is best described as follows;

On a 500 gram basis to make a 4000 ppm concentration of a chelated silver oxide solution suspended in a water/glycerine/PEG base, all materials are weighed out in advance of mixing;

1. Prepare in a separate vessel, distilled (DI ore other suitable filtered water which contains no ions) water, and add chitosan in a concentration of 1-5 weight percent (preferably 2%). Next add an alpha-hydroxy acid—in this case glycolic acid which serves to fully disperse and solubilize the chitosan. Put this slurry solution aside.
2. In a separate vessel prepare an acid solution by taking 5.65 wt. % (28.25 grams) of citric acid and introduce the acid into 5.65% (28.25) grams of distilled water and heat to 82 degrees Centigrade and mix for 3-4 minutes under rapid agitation and continue mixing in the slurry at high speeds (again 1000 rpm or greater) for 3-4 minutes. The pH of this solution should level out at 1.83. Put this solution aside as well.
3. Prepare a third solution of AgO in water by taking 0.47 wt. % (2.35) grams silver oxide powder (nominal particle size distribution is between 4-40 microns)—which in this case is silver oxide (I) from Colonial Metals of Elkton, Md.—and blend at high speed (at least 1000 rpm) into 31.54 wt. % (157.7) grams distilled water (water was used in this case but glycerine and/propanediol and/or PEG could also be used here) at 180 degrees Fahrenheit (82 Centigrade) for up to 3 minutes. The pH of this slurry should rise to at least 8.0 and preferably to between 8.3 and 8.4 (presumably due to the production of AgOH). More than 3 minutes will cause too much oxidation. Put this dark slurry solution aside.

4. Combine solutions (1) and (2) above into a single vessel. Then add the silver oxide solution (3) quickly with a buret (titration-like method) to a slowly stirring solution of (1) and (2) within the single vessel. The ratio of the combined weight of (1) and (2) will be 56.18 weight percent of the final solution and 43.82 weight percent will be that of the AgO solution, which initially are all mixed together at 82 degrees Centigrade. This method will ensure that no silver citrate is formed during the chelation process and is critical to the process. The chelation reaction is extremely rapid (within less than 3 minutes after full addition of the AgO solution (3) to the combined solutions (1) and (2).

5. The temperature is at 82 degrees Centigrade and the reaction appears complete within a few minutes (no evidence of silver powder remains in the solution) and the solution becomes clear. It is possible to neutralize the pH to 7 or above at this stage using, preferably sodium carbonate and/or arginine or a slight amount of NaOH to ensure no ppt occurs. Arginine and other amino acids seem to bind with the chelated oxide complex in solution.

At this point the 500 gm. chelated silver oxide complex is a suspension (acting as a carrier) solution that is homogeneous, stabile, and ready for use. Concentrations of this silver oxide complex are stabile (no precipitate), using this 5 step procedure, to at least 4000 ppm. Forming the precipitate leads to other complex formations of the silver oxide suspension which is to be avoided as the precipitate is not as effective in providing stability leading to the potent antibacterial, antiviral, and/or antimicrobial activity of the suspension which is free of precipitate. Likewise, it is believed that the UV, conductivity, and/or permeability/flammability properties are only constant and reproducible without the formation of precipitate.

In this specific example, the incorporation of 4000 ppm of chelated silver oxide was suspended in a water solution. As previously stated, the use of other polyols, such as glycerine, propanediol, PEG, or even combinations of the any of the polyols with water have also been successfully employed. Once the solution-based complex suspension of steps 1-5 above was formed and stabilized, in this case with a 4000 ppm chelated silver oxide concentration in water, it was possible to successfully incorporate this liquid suspension into the gel composition to accomplish the finished product. Procedure for Providing 1,000 Grams of 250 ppm of the Gel Composition, was Accomplished According to the Following Steps;

1. Take 736.8 grams of Distilled Water (83.98%) at room temperature and introduce slowly, under moderate agitation, 44 grams of Polyquaternium (Celquat H-100)—4.415%. Mix for 5 minutes.
2. Take 115.5 grams of USP Glycerin 99% at room temperature and add to the H2O/Polyquaternium mixture—1.155%. Continue with moderate agitation.
3. Immediately add 24.5 grams of Polyquaternium/Hyaluronic Acid mixture (BHA-10) and continue moderate agitation—2.45%
4. Immediately add 17.5 grams of a 25% Arginine in water solution—1.75%
5. Immediately add 61.5 grams of 4,000 ppm of the chelated silver oxide liquid suspension with chitosan—6.25%

The gel composition will form approximately 10 minutes after the first introduction of polyquaternium in Step 1 above.

To produce 60 kilograms of the gel, it was necessary to produce 3.69 kilograms of the chelated silver oxide liquid suspension using the same methodology required to produce 500 grams. The gel was then accomplished as follows;

1. In a first vessel was filled with 44.211 kg of distilled water and 2.649 kg of a polyquaternium which is cationic (such as Celquat H-100 ® manufactured by Akzo Nobel the U.S. division of which is headquartered in Chicago, Ill.), as well as 6.930 kg. of USP grade organic kosher certified glycerine all of which were dispersed by slow mixing (to avoid forming air bubbles) in the vessel at room temperature. This causes immediate onset of gelation. Next, to the same vessel was added 1.470 kg. of a combination of hyaluronic acid with a polyquaternium polymer (such as BHA-10® manufactured by Koda Corporation of Ontario, Canada). The pH of this solubilized gelling solution after 2-4 minutes of stirring is less than 7.0.
2. In order to raise the pH of the solution the vessel, in a separate vessel, a solution of 75 wt. % distilled water and 25 wt. % arginine is mixed together. 1.040 kg of this solution is then added to the first vessel of step (1) above. This should increase the pH of the solution in in the first vessel to at least 7.4 or above.
3. The third step is then to add, in this case, 3.69 kg of the 4,000 ppm chelated silver oxide complex suspension solution within 10 minutes of completion of step (2) and begin mixing with a planetary (or other suitable) mixer to ensure homogeneity.

In this manner, the entire gelation process is prepared using cationic (positively charged) ionic substances so that a thixotropic gel with no precipitate will result. If anions are present in his portion of the preparation it is likely that precipitates of silver salts will form—which is undesirable. If these salts form, in fact, it will cause the gel to lose a proportion of its thixotropic properties. For the present invention, the term "thixotropic" refers to a time-dependent shear thinning property of the gel. Certain gels or fluids that are thick (viscous) under static conditions will flow (become thin, less viscous) over time when shaken, agitated, or otherwise stressed and are therefore time dependent with regard to the viscosity. They then require a fixed time to return to a more viscous state.

The final gel of the present invention in this particular case contains 250 ppm of the chelated silver oxide complex. As seen in Table 1 below, the gel has been confirmed to completely eliminate the growth of *Escherichi coli* (*E-coli*), *Proteus mirabilis*, *Klebsiella pneumonlae*, *Enterococcus faecalis*, *Pseudenomas aeruginosa* ATCC 27853, *Bacillus cereus* 35, and *Bacillus cereus* ATCC 13061. This testing was performed by an outside laboratory (Schulke, Inc. of 30 Two Bridges Rd., Fairfield, N.J. 07004) using a TS Agar/TTC medium as the culture for initially allowing these bacterium to initially grow. A second culture was prepared using the same medium but with the addition of the final gel composition of the present invention.

TABLE 1

Bacterial Growth Before and After Treatment with Chelated Silver Oxide Complex in Gel (initial concentration 4000 ppm, final concentration 250 ppm in the Gel)

| Microorganism | Without Gel | With Gel (how much Gel?) | Percent Reduction |
|---|---|---|---|
| E-coli | growth red color rxn. | No growth | 100% |
| P. Mirabilis | growth red color rxn. | No growth | 100% |
| K. Pneumonlae | growth red color rxn. | No growth | 100% |
| E. Faecalis | growth weak color rxn | No growth | 100% |
| Pseudomonas aeruginosa ATCC 27853 | growth red color rxn. | No growth | 100% |
| Bacillus cereus 35 | growth red color rxn. | No growth | 100% |
| Bacillus cereus ATCC 13061 | growth red color rxn. | No growth | 100% |
|  | growth red color rxn. | No growth | 100% |

Keeping the metal oxide chelate complex suspended without precipitation (for an indefinite time period—at least many months and up to years) is known to impart the antibacterial properties as given below in Table 2:

TABLE 2

Anti-Bacterial Paint Results for Chelated Silver Oxide in PEG Suspension Complex (initial concentration 2000 ppm, final concentration 100 ppm in the paint)

| Organism | Initial Organism Count in Cultured Suspension Before Exposure PEG Complex | Final Organism Count After Exposure to PEG Complex |
|---|---|---|
| P. aeruginosa | $1.1 \times 10^5$ | 25 CFU |
| S. aureus | $7.0 \times 10^5$ | 412 CFU |
| E. coli | $6.8 \times 10^5$ | 12 CFU |
| C. albicans | $1.0 \times 10^5$ | 199 CFU |
| A. niger | $1.0 \times 10^5$ | 8 CFU |

The results in Table 2 are from the addition of the chelated silver oxide complex at 2000 ppm in a PEG (polyethylene glycol) base that is subsequently added to an interior acrylic semi-gloss paint (product code 240100) in a let-down ratio of 20:1. The final concentration of the silver oxide chelate complex in PEG was only 100 ppm. The paint was then tested to determine the antimicrobial and antibacterial properties as follows;

Using a 9×13 glass dish that was coated with three layers of paint; ⅕ of the area was swabbed with each 105 organism suspension. The organism suspensions were allowed to dry on the surface of the dish for approximately thirty minutes. The surface of the dish was inoculated with P. aeruginosa (ATCC 9027), S. aureus (ATCC 6538), E. coli (ATCC 8739), C. albicans (ATCC 10231) and A. niger (ATCC 16404). Contact slides were placed on the inoculated areas. P. aeruginosa. S. aureus, and E. coli were incubated at 30-35 degrees Celcius for 72 hours and enumerated. C. albicans and A. niger were incubated at room temperature for 5 days.

The data above in Table 2 was taken from a solution that was prepared as follows;

Working Example 2

A 500 ml amount of polyol based complex suspension together with 100 ppm of a silver oxide complex was prepared in the following manner:
Solution A
0.265 gms. Citric Acid and add to
299.735 gms. Distilled Water with 2% chitosan solution Mix 5-10 minutes Slurry 1
0.11 gms. Silver Oxide and add to
99.89 gms. Distilled Water
Disperse 5-10 minutes Take prepared Solution A and place under moderate agitation for the stipulated time. Slowly add the previously dispersed silver oxide in water Slurry 1 and mix at high speed for 30-45 minutes. The resulting silver oxide is a chelate and is colorless and odorless. Remove from agitation, filter through a qualitative analysis filter paper, such as VWR 20 415, and set aside in a light impervious container. The silver oxide complex is now ready to be used to make a glycerine composition useful for various purposes. Take 30 mls of the 2% chitosan solution and to it add 70 mls distilled water. Mix for 1 minute and then add to the 400 mls of the previously prepared 100 ppm chelated silver oxide complex. Mix all for 3 minutes and then add to the polyol such as propanediol and/or glycerine with or without water as a non-precipitating complex suspension to stabilize the suspension solution.

Applicant has found that chelated silver oxide and polyol and/or glycerine when complexed into a gel composition exhibits the needed unique characteristics combining lubricity, processibility, antimicrobial (as well as semi-conductive/conductive, UV resistant, permeability and flammability changing) properties in meeting multi-purpose criteria. The chelated silver or other metal oxide complexes, which are also biocompatible, adds antimicrobial properties into the gels to provide reduction or elimination of contamination by bacteria, fungi, mold, germs, and microbes and in some cases, viruses. There is a body of evidence that suggests the same metal oxide complexes will provide conductive, UV resistant, permeability, and flammability changing properties for the gels and subsequent articles of manufacture utilizing these gels.

Other metal oxide chelates using acids other than citric acid (such as glycolic acid, nitric acid, etc.) are anticipated in the present invention. Using citric and amino acids leads to chelated silver oxides that are ingestible (not toxic) for humans and other mammals. This chelated silver oxide in the form of the gel compositions described above is very safe and effective for exterior application to the skin. It is also possible to provide non-toxic and ingestible as well as "green" and sustainable gel compositions—which also is distinctive from other metal oxide compositions developed by previous investigators.

Additionally, other salts may be added to the composition that do not react in solution but provide some beneficial effect such as stabilization of the suspension, modification of chelated metal oxide ion release rate, promotion of galvanic action, increase in antimicrobial effectiveness, or enhancement of biocompatibility. Further, other compounds may be added to the composition, including, but not limited to, medicinal agents, lubricants, nutritional agents, antioxidants, dyes and pigments, and other additives.

As noted above, any gel can be used to form the compositions of the present invention. When hydrophilic gels are used, it is preferable that the gels be soluble in water or in organic solvents containing some water. The ability to add water to the gel composition without precipitating the polymer allows the addition of water-soluble salts directly. The use of water in the gel composition increases the solubility of the salts, resulting in the formation of finer more stable colloids.

In contrast, when hydrophobic gels are used either alone or in combination with hydrophilic gels, it is desirable to limit the amount of water present in the composition to avoid precipitation of the hydrophobic components of the gel. In such instances the amount of water present in the gel composition is preferably 10% or less. Thus, when hydrophobic gels are employed in the present invention, the preferred water content of the gel compositions is between about 1 and 20% by weight. It is advantageous to employ salts that are soluble in alcohols or organic solvents when hydrophobic gels are employed.

Polyols useful as solute-like suspension agents for the chelated silver oxide include, but are not limited to, polyethylene glycols, polyester polyols, polyether polyols, castor oil polyols, and polyacrylate polyols, including Desmophen A450, Desmophen A365, and Desmophen A160 (available from Mobay Corporation), poly(ethylene adipates), poly(diethyleneglycol adipates), polycaprolactone diols, polycaprolactone-polyadipate copolymer diols, poly(ethyleneterephthalate)diols, polycarbonate diols, polytetramethylene ether glycol, ethylene oxide adducts of polyoxypropylene diols, and ethylene oxide adducts of polyoxypropylene triols.

The chelated silver oxide solution of the present invention can be further processed for a wide variety of dispensing methods, but for the purposes of the present disclosure a dispersion into a glycerine, PEG and/or water base is provided.

The present disclosure also relates to an antimicrobial topical composition comprising complexes of chelated metal oxides and more specifically, a version utilizing chitosan-silver oxide, and in particular to solutions comprising complexed chitosan-silver oxide bio-films, and to the methods of making the same to form a polyol based dispersion of chelated silver oxide suspensions that can be compounded or blended with gelled substances, yielding antibacterial compounds with essentially imperceptible changes in physiochemical properties when processed. The use of chitosan to make the chelated metal oxide complex suspension is helpful in that it imparts biofilm properties to the complex useful for application to mammalian skin.

For this embodiment, the chitosan solution is formed by first providing chitin, which is a homopolymer of beta (1-4)-linked N-acetyl-D-glucosamine. Rinsed, dried and ground chitin can then undergo a process of deacetylation to convert some N-acetyl glucosamine to glucosamine, a primary component of chitosan. The chitosan solution can then be prepared by mixing chitosan with an alpha-hydroxy acid such as glycolic acid and allowing it to thicken. A silver solution can be prepared by mixing silver oxide with a combination of a carboxylic acid and the chitosan solution (such as citric acid) to form silver oxide chelate. Since the chitosan solution is cationic, and the silver solution may be generally neutral, the resulting silver-oxide chitosan complex will be primarily cationic. The cationic solution of the present invention will bond nicely with the generally negatively charged human skin. In use, citrate helps promote uptake of the silver by bacteria.

According to one advantage of the present invention, an antimicrobial solution having high immediate and short term effectiveness is provided. This is accomplished as bacteria are attracted to the citrate in the solution. The citrate promotes uptake of the silver oxide ion in the bacteria, resulting in effective killing of the bacteria. In fact, as shown in Tables 1 and 2 above and other data obtained from independent test laboratories, the present invention comprising the chitosan-silver oxide complex has been evaluated to be effective against *Salmonella*, *E-coli*, MRSA (staph), *Pseudomonas aeroginosa*, *Serratia marcescens* and *Klebsiella pnuemoniae*.

According to another advantage of the present embodiment, an antimicrobial solution having high residual effectiveness and stability is provided. This is accomplished as the antimicrobial solution can be prepared to not only be relatively stable but also exhibit low volatility and does not readily evaporate. In part this is due to the hydration of the silver oxide powder in deionized water (distilled or other suitably filtered water free of ions) prior to any chelation and the fact that this causes the silver oxide powder to form a thin and eventually alkaline slurry—again prior to any chelation and before the addition of the chitosan and carboxylic acid. Using certain alkaline substances that will enlarge the chelated metal oxide particles are not appropriate in that this will cause premature precipitation.

Related and according to a further advantage of the embodiment, an antimicrobial silver oxide solution that readily bonds to a user's skin such that it remains in place is provided. This is accomplished because in this silver oxide complex suspension, the silver oxide is further bonded to the chitosan to further form a biofilm forming complex and thus forms a molecule that is positively charged or cationic. The skin of the human body typically exhibits a negative charge and accordingly is anionic. The natural electrostatic attraction of the chitosan-silver oxide complex to the surface of the skin allows the complex to bond with the skin. In fact, laboratory results have shown a 100 ppm chitosan-silver oxide complex to have a residual efficacy of greater than 24 hours under laboratory conditions. This is achieved without the use of synthetics and without the utilization of alcohol, benzalkonium chloride or triclosan. The chelated silver oxide component is the active ingredient that quickly dispatches the bacteria upon contact with the intended surface and also provides unsurpassed biocompatibility qualities not seen for other chelated silver complexes. This is primarily due to the fact that the silver oxide is stabilized in an alkaline medium prior to chelation and complexing.

According to a still further advantage, an antimicrobial silver oxide alkaline based solution that is stable, portable and easily dispensable is provided. The stabilization of the silver oxide in an aqueous alkaline medium suspension is a complex that further provides both instant biocompatibility and antimicrobial action with most undesirable bacterial, mold and/or fungal organisms at a cellular level. There is recent evidence that silver oxides actually are effective in providing cellular changes through the DNA and by chelation it is believed that the silver oxide of the present invention allows for superior intracellular activity when compared with other known liquid or solid forms of silver (or any metal) oxide—especially that of colloidal metal oxides.

Other advantages, benefits, and features of the present invention will become apparent to those skilled in the art upon reading the detailed description of the invention and studying the drawings.

BRIEF DESCRIPTION OF THE DRAWINGS

FIG. 1 is a flow chart showing a preferred embodiment of the process of making a chitosan solution.

FIG. 2 is a flow chart showing a preferred embodiment of the process of making the chelated silver oxide suspension in solution, which can be applied to most other metal oxides.

FIG. 3 is a flow chart showing a preferred embodiment of the process of preparing one of the AgO containing gel compositions of the present invention.

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

A process of forming chitosan is provided. Raw material also provided. The raw material is chitin. Chitin is a homopolymer of beta (1-4)-linked N-acetyl-D-glucosamine. Chitin is an abundant naturally occurring and renewable resource bio-polymer. Chitin is found in exoskeletons of invertebrates. In a preferred embodiment, chitin is derived from the family of decapod crustaceans such as shrimp and prawns. Chitin obtained in this manner generally has a molecular weight of approximately between 500 and 900 kDalton. These steps are necessary to the present invention as chitin is insoluble.

The chitin is processed by removing non-chitin components. This step is accomplished in one embodiment through the use of hydrochloric acid (HCL). The HCL removes or strips any residual meat tissue that is attached to the shell. It is appreciated that other acids or methods of stripping the residual meat tissue can be incorporated without departing from the broad aspects of the present invention. After the residual meat tissue is stripped, a solution of Sodium Hydroxide (NaOH) is used to rinse and neutralize the exoskeletons. In the preferred embodiment, a NaOH solution of approximately 20% is used.

The chitin is dried and processing the chitin to have a desired size. Preferably, the chitin is ground so that it has an average size of approximately 24 mesh (0.0278 inches average particle dimension).

Deacetylation, next, involves in a preferred embodiment mixing 1 part chitin with 4 parts 50% NaOH, which is a base to which had been added 1 part of pure water. The resulting mixture comprises 5 parts total, of which the solution has 40% NaOH per 1 part chitin. The mixture is heated to approximately 70 degrees Celsius for about 72 hours to undergo the process of deacetylation. The process of deacetylation converts some of the N-acetyl glucosamine to glucosamine. The result of deacetylation is the aggregation and precipitation of chitosan molecules.

The chitosan is removed to remove remaining NaOH and any other impurities. In the preferred embodiment, the step of rinsing the chitosan comprises a triple rinse. Yet, it is appreciated that other numbers of rinses could alternatively be used without departing from the broad aspects of the present invention. It is preferable that the chitosan is then allowed to dry.

Turning now to FIG. 1, the step 10 of making a 2% chitosan solution is provided.

The following preferred embodiment yields approximately 1 liter, or 1000 mls of the chelated silver oxide complex. The first step (11) in this process (10) is to provide deionized water. 182 ml. of deionized water is measured and placed under moderate to high agitation. 20 grams of chitosan (rinsed and dried) is then provided in step (12), and measured. The chitosan powder is dispersed into and mixed with the deionized water under moderate to high agitation. Next, in step (13), an alpha-hydroxy acid such as glycolic acid is provided. In the preferred embodiment, glycolic acid is used for its lack of strong odor, and is of approximately 70% purity. It is understood that other alpha-hydroxy acids may be used without departing from the broad aspects of the present invention. Approximately 45 ml. of the glycolic acid can be added, and the mixture can be mixed slowly for approximately an additional 45 to 60 minutes. After this period of time, the mixture is preferably viscous. The chitosan solution is preferably ready when it achieves the desired viscosity.

Turning now to FIG. 2, a method (20) of preparing a silver oxide solution is provided. First, in step (21), silver salts can be provided. Primarily, the use of silver oxide in a powdered form is provided. Next, an alkaline aqueous solution of water and the silver oxide powder is provided in step (22). The result, in step (23), is the formation of silver oxide in the form of an aqueous alkaline solution. Once the silver oxide thin slurry is created and fully formed, citric acid can be provided together with the thicker chitosan solution (in step 24), and deionized water can be provided in step 25.

The following steps are utilized to yield a 1 liter, or 1000 ml batch of constituted 1000 ppm chelated silver oxide solution. Slurry 1 is prepared by adding approximately 1.10 grams chelated silver oxide to approximately 198.9 grams distilled water and dispersing for approximately 5-10 minutes. The dispersed chelated silver oxide in water Slurry 1 can be slowly added to a solution of the chitosan and citric acid to form a second solution (2) mixed at a high speed for approximately 30-45 minutes. The resulting silver oxide chelate is colorless and odorless. Remove from agitation, filter through a qualitative analysis filter paper, such as VWR, 415 and set aside in a light impervious container (in step 26).

The silver is first dispersed in the distilled water to form a thin slurry so that there is a larger exposure of the surface area of the silver to form a silver oxide molecule which can combine with the citric acid. The $Ag_2O$ molecule is only slightly soluble in a solution; hence the addition of citric acid to the mixture also increases solubility with the chitosan to produce a silver ion portion of the silver oxide compound that forms a coordination compound as a result of a Lewis acid-base reaction. The silver ion here is the acid (acceptor) and the chitosan/citric acid solution acts as a ligand base (donor).

In particular the formed solution is a bio-film forming sanitizer that is cationic and bio-adhesive, and contains chelated silver oxide in a concentration sufficient to effect residual antibacterial activity for hours. Once added to a gel composition as described above, the solution imparts the same properties by infusion of the chelated silver oxide into the final gel composition.

FIG. 3 provides a method (30) of infusing an antimicrobial complex into a gel in order to prepare the chelated metal oxide gel compositions of the present disclosure.

The following ratios are used in order to achieve a 1 liter batch, or 1000 ml. batch. First, in steps approximately 500 ml. of 2% chitosan solution and approximately 400 ml. of deionized water are provided which includes citric acid. The chitosan, citric acid and deionized water are preferably mixed slowly for approximately 3 minutes (steps 31 & 32). Next, approximately 100 ml. of the 1000 ppm silver oxide solution is provided (step 33). The silver oxide solution is added to the chitosan solution and the solution is preferably mixed slowly for an additional 3 minutes (step 34). The resulting solution is a formulation containing 100 ppm silver oxide and bio-bonding chitosan. It is appreciated that all vessels and agitators in this method are made of high density plastic or glass, and must be free of metallic surfaces. The resulting solution is added to a gel composition (step 35), as provided in the discussion of the procedure for providing 1,000 Grams of 250 ppm of the gel composition above.

It is understood that other ratios of chitosan solution to silver oxide solution can be used without departing from the broad aspects of the present invention.

According to the present invention, the citrate is complexed with silver ions and silver oxide and chitosan, and the bacteria accordingly take up the silver oxide citrate chitosan complex. Unwanted bacteria, viruses, molds and fungi rapidly die after taking up the silver, as the silver immediately disables vital proteins and the bacteria's metabolic and reproductive functions and the organisms tend to die within minutes. This chelated silver oxide compound, however, provides biocompatibility with desirable cells and organisms such that there are no known toxic side effects when using the chelated silver oxide complex processed as detailed above.

The silver oxide complex is cationic and bonds readily to negatively charged human or animal skin without any toxic effects. The chitosan-silver oxide complex does not cause silver poisoning in a manner such as is known for many of the colloidal (ionic) silver compounds. This is due to the mechanism of the molecule itself. When absorbed into the skin, the complex immediately becomes inert as it binds with free sodium ions that occur naturally in our bodies and on our skin and the oxygen species acts as primarily to promote stable and healthy cell growth. The chelated silver oxide molecule is eventually excreted through the kidneys or out of the pores of the skin depending on the activity level of the individual.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A homogeneous aqueous gel composition comprising:
   an aqueous solution comprising glycerine, water and a chitosan-metal oxide chelate complex; and
   a cationic gel,
   wherein the aqueous solution is homogeneously suspended in the cationic gel,
   wherein the chitosan-metal oxide chelate complex is cationic and is a coordination compound,
   wherein the chitosan-metal oxide chelate complex comprises a metal oxide chelate and chitosan and the metal oxide chelate is a metal carboxylate complex, and
   wherein the chitosan-metal oxide chelate complex is homogeneously suspended in the aqueous solution.

2. The homogeneous aqueous gel composition of claim 1, wherein said homogeneous aqueous gel composition does not form a precipitate of metal oxide chelate.

3. The homogeneous aqueous gel composition of claim 1, wherein the metal of said metal oxide chelate is selected from the group consisting of silver, copper, zinc, titanium, gold, nickel, and tin.

4. The homogeneous aqueous gel composition of claim 1, further comprising a thickener.

5. The homogeneous aqueous gel composition of claim 1, wherein the concentration of the chitosan-metal oxide chelate complex is about 10 ppm to about 4000 ppm in said gel composition.

6. The homogeneous aqueous gel composition of claim 1, further comprising a biopolymer.

7. A pool product, a spa product, a grout, a sealant, a beverage item, a food item and/or a personal care product comprising the homogeneous aqueous gel composition of claim 1.

8. The homogeneous aqueous gel composition of claim 1, further comprising one or more of an alginate, a dextran, a carrageenan, a pectin, xanthan gum, and/or combinations thereof.

9. A homogeneous aqueous gel composition comprising:
   an aqueous solution comprising water, polyol, and a chitosan-metal oxide chelate complex; and
   a cationic gel,
   wherein the aqueous solution is homogeneously suspended in the cationic gel,
   wherein the chitosan-metal oxide chelate complex is cationic and is a coordination compound,
   wherein the chitosan-metal oxide chelate complex comprises a metal oxide chelate and chitosan and the metal oxide chelate is a metal carboxylate complex, and
   wherein the chitosan-metal oxide chelate complex is homogeneously suspended in the aqueous solution.

10. The homogeneous aqueous gel composition of claim 9, wherein the polyol is selected from the group consisting of glycerine, propanediol, and/or polyethylene glycol.

11. The homogeneous aqueous gel composition of claim 9, wherein said homogeneous aqueous gel composition does not form a precipitate.

12. The homogeneous aqueous gel composition of claim 9, wherein the metal of the metal oxide chelate is selected from the group consisting of silver, copper, zinc, titanium, gold, nickel, and tin oxide.

13. The homogeneous gel composition of claim 9, further comprising a thickener.

14. The homogeneous gel composition of claim 9, wherein the concentration of the chitosan-metal oxide chelate complex is about 10 ppm to about 4000 ppm in said gel composition.

15. The homogeneous gel composition of claim 9, further comprising a biopolymer.

16. A pool product, a spa product, a grout, a sealant, a beverage item, a food item and/or a personal care product comprising the homogeneous aqueous gel composition of claim 9.

17. The homogeneous gel composition of claim 9, further comprising one or more of an alginate, a dextran, a carrageenan, a pectin, xanthan gum, and/or combinations thereof.

18. The paint, pool product, spa product, grout, sealant, beverage item, food item and/or personal care product of claim 16, wherein the personal care product is a shampoo, a hair gel, a lip balm, and/or a hand sanitizer.

19. The homogeneous gel composition of claim 9, wherein said gel is ingestible for humans.

20. A beverage or food item comprising the homogeneous gel composition of claim 9.

21. An article of manufacture comprising the homogeneous gel composition of claim 9.

22. A seafood product comprising the homogeneous gel composition of claim 9 to ensure the reduction or elimination of bacterial growth in storage of seafood.

23. The paint, pool product, spa product, grout, sealant, beverage item, food item and/or personal care product of claim 7, wherein the personal care product is a shampoo, a hair gel, a lip balm, and/or a hand sanitizer.

24. The homogeneous aqueous gel composition of claim 1, further comprising hyaluronic acid, polyquaternium, L-arginine and/or a polymeric disaccharide.

25. The homogeneous aqueous gel composition of claim 24, wherein the polymeric disaccharide is hyaluronic acid.

26. The homogeneous aqueous gel composition of claim 1, wherein the composition is antimicrobial, antibacterial, and/or anti-viral.

27. The homogeneous aqueous gel composition of claim 1, wherein the composition is semi-conductive.

28. The homogeneous aqueous gel composition of claim 9, wherein the composition is antimicrobial, antibacterial, and/or anti-viral.

29. The homogeneous aqueous gel composition of claim 9, wherein the composition is semi-conductive.

* * * * *